(12) United States Patent
Peltz et al.

(10) Patent No.: US 10,188,103 B2
(45) Date of Patent: Jan. 29, 2019

(54) ANTIMICROBIAL COATING FABRICATION METHOD AND STRUCTURE

(75) Inventors: Leora Peltz, Pasadena, CA (US); Ji Hye Son, Rowland Hgts., CA (US); Shawn Hyunsoo Park, Cerritos, CA (US); Rovelyn T. Dytioco, Seattle, WA (US)

(73) Assignee: THE BOEING COMPANY, Chicago, IL (US)

( * ) Notice: Subject to any disclaimer, the term of this patent is extended or adjusted under 35 U.S.C. 154(b) by 2088 days.

(21) Appl. No.: 12/211,030

(22) Filed: Sep. 15, 2008

(65) Prior Publication Data

US 2010/0068236 A1    Mar. 18, 2010

(51) Int. Cl.
*A01N 25/34*    (2006.01)
*B33Y 10/00*    (2015.01)

(52) U.S. Cl.
CPC ..................... *A01N 25/34* (2013.01)

(58) Field of Classification Search
CPC ........... A01N 25/34; A01N 61/00; B05D 5/08
USPC .................. 427/446; 424/411–415
See application file for complete search history.

(56) References Cited

U.S. PATENT DOCUMENTS

| | | | |
|---|---|---|---|
| 3,755,713 A | 8/1973 | Paszkowski | |
| 4,502,092 A | 2/1985 | Bannik, Jr. et al. | |
| 4,912,594 A | 3/1990 | Bannik, Jr. et al. | |
| 5,490,962 A * | 2/1996 | Cima et al. | 264/401 |
| 5,538,732 A | 7/1996 | Smith et al. | |
| 6,068,911 A | 5/2000 | Shouji et al. | |
| 6,723,428 B1 * | 4/2004 | Foss et al. | 428/370 |
| 6,986,853 B2 | 1/2006 | Glatkowski et al. | |
| 7,307,825 B2 | 12/2007 | De La Fuente De Ana et al. | |
| 7,364,756 B2 | 4/2008 | Gabbay | |
| 7,935,214 B2 | 5/2011 | Gammon et al. | |
| 8,057,888 B2 | 11/2011 | Gammon et al. | |
| 8,512,507 B2 | 8/2013 | Gammon et al. | |
| 2003/0091767 A1 | 5/2003 | Podhajny | |
| 2003/0113520 A1 | 6/2003 | Takahashi et al. | |
| 2003/0170453 A1 * | 9/2003 | Foss et al. | 428/373 |
| 2004/0115167 A1 | 6/2004 | Cormier et al. | |
| 2004/0156918 A1 | 8/2004 | Podhajny | |
| 2005/0203237 A1 | 9/2005 | Cornelius Maria Dekkers et al. | |
| 2005/0208275 A1 | 9/2005 | Abe et al. | |
| 2005/0228477 A1 | 10/2005 | Grainger et al. | |
| 2006/0024508 A1 | 2/2006 | D'Urso et al. | |
| 2006/0035039 A1 * | 2/2006 | Ylitalo et al. | 428/32.22 |
| 2006/0153993 A1 | 7/2006 | Schmidt et al. | |
| 2006/0292208 A1 * | 12/2006 | Vachon | 424/445 |
| 2007/0227428 A1 | 10/2007 | Brennan et al. | |
| 2007/0232166 A1 | 10/2007 | Hayashi et al. | |
| 2007/0292486 A1 | 12/2007 | Sen et al. | |
| 2008/0145528 A1 | 6/2008 | Deng et al. | |
| 2010/0316844 A1 | 12/2010 | Park et al. | |

FOREIGN PATENT DOCUMENTS

| | | |
|---|---|---|
| DE | 10014486 | 10/2001 |
| EP | 0568322 | 11/1993 |
| EP | 0633327 | 1/1995 |
| EP | 0719594 | 7/1996 |
| EP | 2168432 | 3/2010 |
| EP | 2319632 | 5/2011 |
| JP | S57137549 | 8/1982 |
| JP | H11300921 | 2/1999 |
| JP | 2001096674 | 4/2001 |
| JP | 2001152051 | 6/2001 |
| JP | 2003211569 | 7/2003 |
| JP | 2003213897 | 7/2003 |
| JP | 2005205378 | 8/2005 |
| JP | 2007270378 | 10/2007 |
| JP | 2007289873 | 11/2007 |
| JP | 2008180003 | 8/2008 |
| JP | 2008183482 | 8/2008 |
| JP | 2008238440 | 10/2008 |
| JP | 2008265236 | 11/2008 |
| WO | 0041530 | 7/2000 |
| WO | 03039766 | 5/2003 |
| WO | 2004030743 | 4/2004 |
| WO | 2005014742 | 2/2005 |
| WO | 2007147094 | 12/2007 |

OTHER PUBLICATIONS

"Mechanochemistry of zeolites: Part 2. Change in particulate properties of zeolites during ball milling", Zeolites, 1995, 15, 252-247.*
Cho, W., et al. "Methods for distributed design and fabrication of parts with local composition control." Proceedings of the 2001 NSF Design and Manufacturing Grantees Conference. 2001.*
European Search Report 09170242.3, The Boeing Company, dated Feb. 26, 2010.
Schumacher, James F. et al "Species-Specific Engineered Antifouling Topographies: Correlations Between the Settlement of Algal Zoospores and Barnacle Cybrids," Biofouling, 2007, 23(5): 307-317.
Schumacher, James F. et al "Engineered Antifouling Microtopographies—Effect of Feature Size, Geometry, and Roughness on Settlement of Zoospores of the Green Alga Ulva," Biofouling, 2007, 23(1): 55-62.
Feinberg, Adam W. et al. "Systematic Variation of Microtopography, Surface Chemistry and Elastic Modulus and the State Dependent Effect on Endothelial Cell Alignment," Wiley InterScience (www.interscience.wiley.com) DOI: 10.1002/jbm.a.31626, Nov. 9, 2007, 13 pages.
Bohannon, John "Smart Coatings Research Shows the Virtues of Superficiality," Science www.sciencemag.org, vol. 309, Jul. 15, 2005, 2 pages.

(Continued)

*Primary Examiner* — Bethany P Barham
*Assistant Examiner* — Peter Anthopolos
(74) *Attorney, Agent, or Firm* — Hanley, Flight and Zimmerman, LLC

(57) ABSTRACT

An antimicrobial coating fabrication method includes providing a substrate having a substrate surface, providing at least one first antimicrobial material in at least one first pattern on the substrate surface and providing at least one second antimicrobial material on the substrate surface in at least one second pattern disposed in generally adjacent relationship with respect to the at least one first pattern of the first antimicrobial material. An antimicrobial structure is also disclosed.

22 Claims, 3 Drawing Sheets

(56) References Cited

OTHER PUBLICATIONS

United States Patent and Trademark Office, "Final Office Action," issued in connection with U.S. Appl. No. 12/609,352, dated Jul. 1, 2011, 20 pages.
United States Patent and Trademark Office, "Non-Final Office Action," issued in connection with U.S. Appl. No. 12/609,352, dated Feb. 18, 2011, 22 pages.
Gardiner, "Lightning Strike Protection for Composite Structures," High Performance Composites, Jul. 1, 2006, [http://www.compositesworld.com/articles/lightning-strike-protection-for-composite-structures], retrieved on Jun. 24, 2015, 8 pages.
European Search Report, "Extended Search Report," issued in connection with European Patent Application 10188345.2, dated Jan. 28, 2011, 9 pages.
European Patent Office, "Communication Pursuant to Article 94(3) EPC," issued in connection with European Patent Application No. 10188345.2, dated Nov. 7, 2017, 8 pages.
United States Patent and Trademark Office, "Decision on Appeal," issued in connection with U.S. Appl. No. 12/609,352, dated Jan. 16, 2018, 20 pages.
European Patent Office, "Communication Pursuant to Article 94(3) EPC," issued in connection with European Patent Application No. 09170242,3, dated Aug. 4, 2016, 3 pages.
European Patent Office, "Communication Under Rule 71(3) EPC," issued in connection with European Patent Application No. 09170242.3, dated May 2, 2017, 60 pages.
Schumacher, et al., "Engineered nanoforce gradients for inhibition of settlement (attachment) of swimming algal spores," American Chemical Society, Mar. 25, 2008, [http:/fwww.researchgate.net/ publi cation/5489925_Engineered_n an oforce_gradients_f or_inhibition_ of_s ettlement_% 28attachment%29_of_swimming_algal_spores], retrieved on Jul. 14, 2015, 8 pages.
Hoowaki, "Hookwaki Technology," [http://www.hoowaki.com/], retrieved on Jul. 15, 2015, 1 page.
Cannon et al., "Hydrophobicity of curved microstructured surfaces," Journal of Micromechanics and Microengineering, vol. 20, Jan. 18, 2010, [http://www.hoowaki.com/files/research/2010-jmm-hydrophobic-curved.pdf], retrieved on Jul. 15, 2015, 6 pages.
Cannon et al., "Visualizing contact line phenomena on microstructured superhydrophobic surfaces," Journal of Vacuum Science and Technology, vol. 28 (3), May 2010, [http://www.hoowaki.com/files/research/2010-jvst-droplet.pdf], retrieved on Jul. 15, 2015, 4 pages.
United States Patent and Trademark Office, "Examiner's Answer to Appeal Brief," issued in connection with U.S. Appl. No. 12/609,352, dated Aug. 1, 2016, 17 pages.
United States Patent and Trademark Office, "Final Office Action," issued in connection with U.S. Appl. No. 12/609,352, dated Jul. 17, 2015, 25 pages.
United States Patent and Trademark Office, "Non-final Office Action," issued in connection with U.S. Appl. No. 12/609,352, dated Oct. 29, 2014, 41 pages.
United States Patent and Trademark Office, "Advisory Action," issued in connection with U.S. Appl. No. 12/609,352, dated Nov. 5, 2015, 7 pages.
United States Patent and Trademark Office, "Requirement for Restriction," issued in connection with U.S. Appl. No. 12/609,352, dated Jan. 25, 2011, 7 pages.
Japanese Patent Office, "Search Report by Registered Searching Organization," issued in connection with Japanese Patent Application No. 2009-211168, dated May 22, 2013, 13 pages (includes English translation).
Japanese Patent Office, "Notification of Reasons for Refusal," issued in connection with Japanese Patent Application No. 2009-211168, dated May 28, 2013, 6 pages (includes English translation).
Japanese Patent Offace, "Notification of Reasons for Refusal," issued in connection with Japanese Patent Application No. 2009-211168; dated Jun. 12, 2014, 8 pages (includes English translation).
Japanese Patent Office, "Decision to Grant a Patent," issued in connection with Japanese Patent Application No. 2009-211168, dated Apr. 27, 2015, 6 pages (includes English translation).
Japanese Patent Office, "Search Report by Registered Searching Organization," issued in connection with Japanese Patent Application No. 2010-243051, dated Jul. 17, 2014, 11 pages (includes English translation).
Japanese Patent Office, "Notification of Reasons for Refusal," issued in connection with Japanese Patent Application No. 2010-243051, dated Jul. 25, 2014, 6 pages (includes English translation).
Japanese Patent Office, "Decision to Grant a Patent," issued in connection with Japanese Patent Application No, 2010-243051, dated Feb. 16, 2015, 5 pages (includes English translation).

* cited by examiner

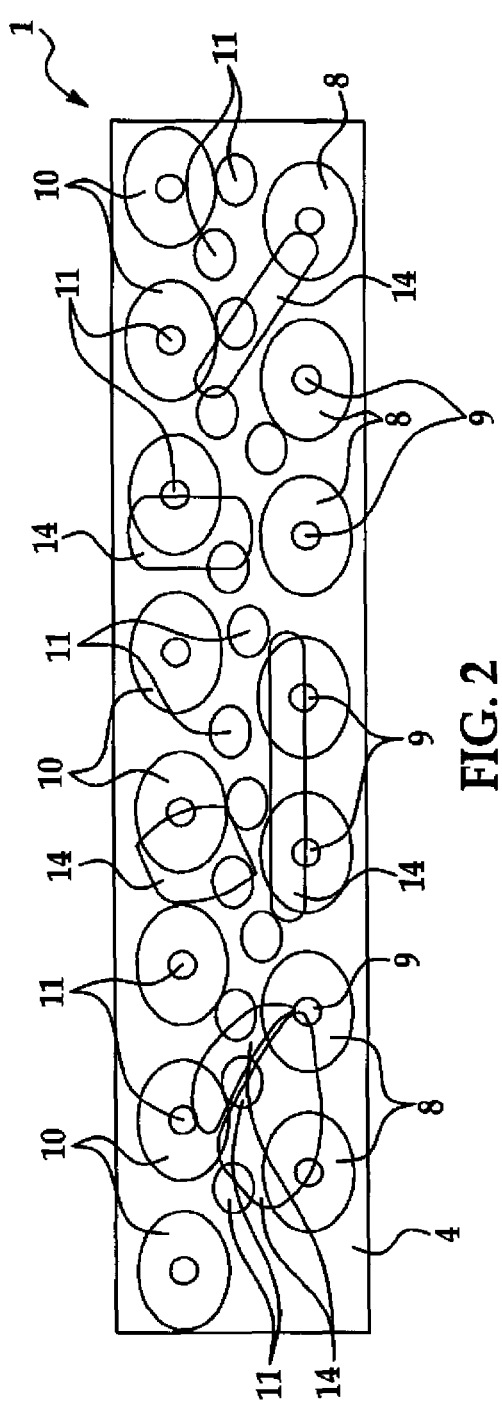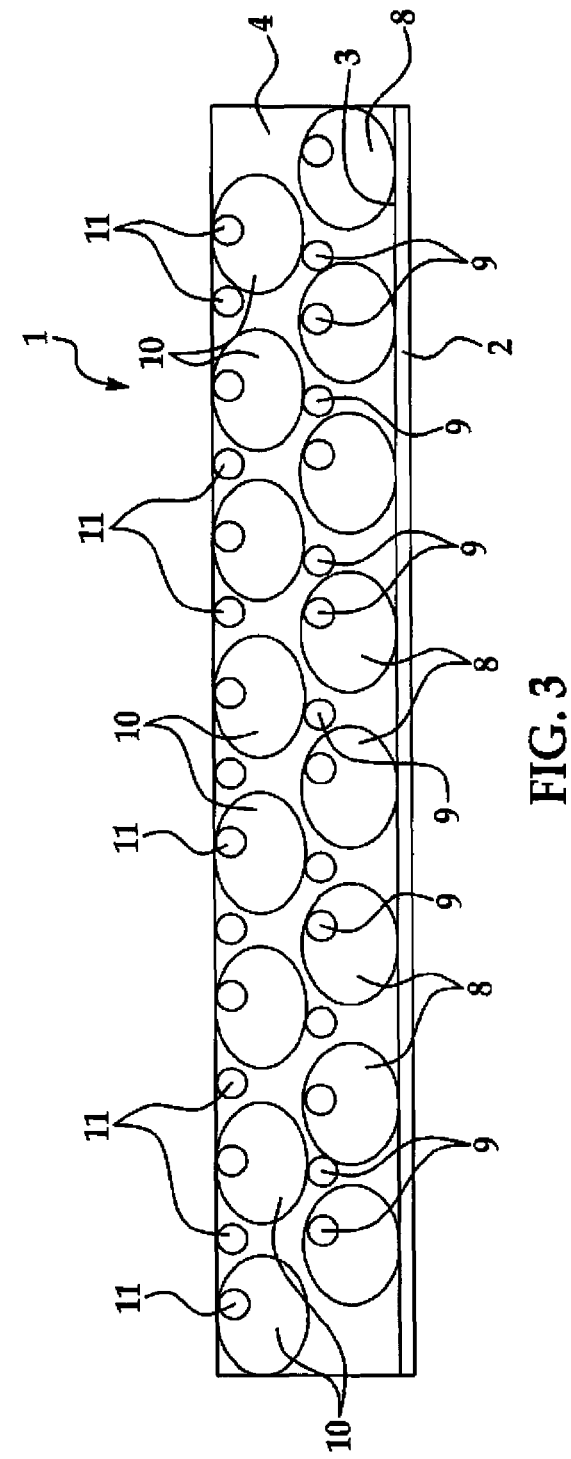

ANTIMICROBIAL COATING FABRICATION METHOD AND STRUCTURE

TECHNICAL FIELD

The disclosure relates to materials and structures having antimicrobial properties and methods of fabricating antimicrobial surface coatings. More particularly, the disclosure relates to an antimicrobial coating fabrication method and structure in which an antimicrobial coating may be applied to a surface in such a manner that different antimicrobial materials in the coating may remain unmixed to substantially retain or optimize the full antimicrobial efficacy of the materials.

BACKGROUND OF THE INVENTION

Various antimicrobial materials and coatings are known. In fabrication of an antimicrobial plastic product, a single biocide may be added to a plastic resin which may then be blended, melted and molded or extruded into the final product. In fabrication of a fabric having antimicrobial properties, a single biocide (which may be a well-known biocide or a biocide which is currently in research, such as a fullerance, for example and without limitation), may be added to a fabric substrate by foaming, padding or spraying. In fabrication of ionic antimicrobial agents (such as silver ions, for example), the ions may be embedded in a zeolite structure. Recent developments in nanotechnology have enabled embedding of silver ions in various materials such as fabric and plastic, for example. During the preparation process, silver nanoparticles may be immobilized on fibers using the layer-by-layer deposition method. This step may involve dipping or treatment of the fibers in various solutions.

The antimicrobial efficacy of an antimicrobial coating may be limited by the use of a single type of antimicrobial material in the coating. Moreover, the mixing of various antimicrobial agents in a resin may neutralize or precipitate the agents, possibly resulting in a less potent antimicrobial coating or structure than would be attained using a single antimicrobial agent. Combining of multiple types of antimicrobial materials in a selected pattern on a surface of a structure or in a coating, and optimization of the geometric parameters of the pattern, may optimize the antimicrobial efficacy of the antimicrobial materials.

Therefore, an antimicrobial coating deposition method and structure is needed in which the geometric parameters of a pattern of antimicrobial materials in a coating may be controlled at multiple scales of magnitude to optimize the antimicrobial efficacy of two or more of the antimicrobial materials in the coating.

SUMMARY OF THE INVENTION

The disclosure is generally directed to a method of fabricating an antimicrobial surface coating. An illustrative embodiment of the method includes providing a substrate having a substrate surface, providing at least one first antimicrobial material in at least one first pattern on the substrate surface and providing at least one second antimicrobial material on the substrate surface in at least one second pattern disposed in generally adjacent relationship with respect to the at least one first pattern of the first antimicrobial material.

The disclosure is further generally directed to an antimicrobial structure. An illustrative embodiment of the antimicrobial structure includes a substrate having a substrate surface, at least one first antimicrobial material provided in at least one first pattern on the substrate surface and at least one second antimicrobial material provided on the substrate surface in at least one second pattern disposed in generally adjacent relationship with respect to the at least one first pattern of the first antimicrobial material.

BRIEF DESCRIPTION OF THE ILLUSTRATIONS

FIG. 2 is a top view of an illustrative embodiment of the antimicrobial structure in which antimicrobial materials are applied to a surface of a substrate in a coating according to geometrical parameters which optimize the antimicrobial efficacy of the materials.

FIG. 3 is a side view of an illustrative embodiment of the antimicrobial structure shown in FIG. 2.

DETAILED DESCRIPTION OF THE INVENTION

Figure 1:
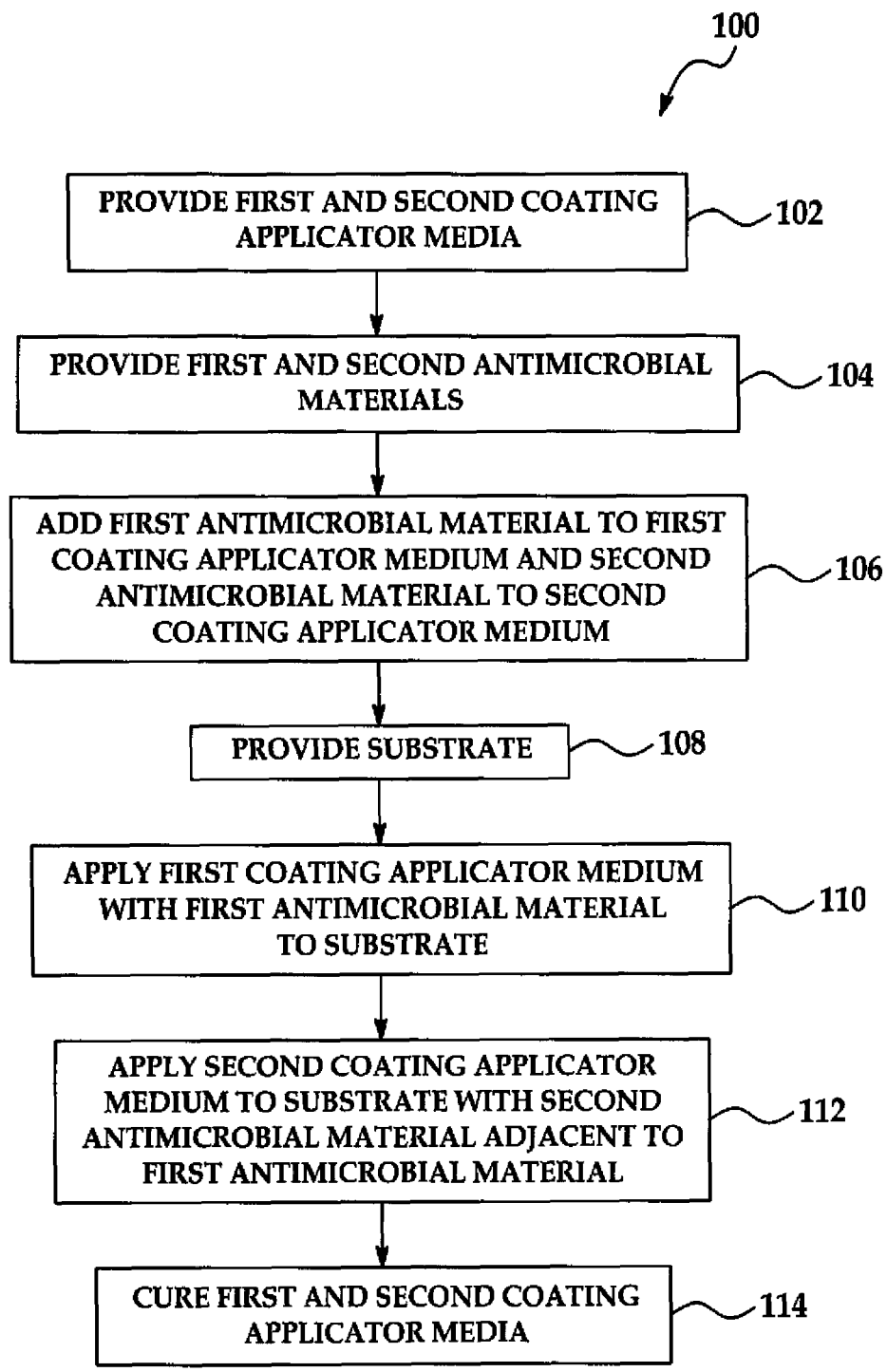
FIG. 1 is a flow diagram of an illustrative embodiment of a method of fabricating an antimicrobial surface coating.

The disclosure is generally directed to a method of fabricating an antimicrobial surface coating. In some embodiments the method may include, for example and without limitation, providing at least first and second coating applicator media; providing at least first and second antimicrobial materials; adding the first antimicrobial material (such as $TiO_2$, Ag, fullerances and/or $H_2O_2$, for example and without limitation) to the first coating applicator medium and the second antimicrobial material to the second coating applicator medium; providing a substrate having a surface; applying the first coating applicator medium with the first antimicrobial material to the surface of the substrate; applying the second coating applicator medium with the second antimicrobial material to the surface of the substrate with the second antimicrobial material adjacent to the first antimicrobial material; and curing the first and second coating applicator media. In some embodiments the first coating applicator medium, the second coating applicator medium and any additional coating applicator medium may be successively applied to the surface of the substrate using any suitable three-dimensional printing technique which is known to those skilled in the art to disperse or distribute the first, second and any additional antimicrobial material in a multi-layered, three-dimensional pattern in the antimicrobial surface coating. In some embodiments, the three-dimensional printing technique which is used to apply the first and second and any additional coating applicator media to the surface of the substrate may include ink jet printing, for example and without limitation.

The disclosure is further generally directed to an antimicrobial structure which may include an antimicrobial coating applied to a surface as a pattern (which may be a random distribution, an organized distribution or both a random distribution and an organized distribution) in which different antimicrobial materials remain substantially unmixed to retain or optimize the full antimicrobial efficacy of the materials. The three-dimensional geometric parameters of the pattern of antimicrobial materials in the structure or coating may be controlled at multiple scales of magnitude to optimize the antimicrobial efficacy of the antimicrobial materials. Accordingly, the various antimicrobial materials may be dispersed in substantially adjacent relationship with respect to each other in the pattern at spacings which may vary from microns to one millimeter, for example and without limitation, optimizing the antimicrobial efficacy of the coating. The antimicrobial materials may be applied separately and successively in a layer-by-layer pattern to the surface to substantially maintain separation of the materials from each other in the pattern. In some embodiments, the first coating applicator medium and the second coating applicator medium may be applied to the surface of the substrate using any suitable three-dimensional printing technique which is known to those skilled in the art. In some embodiments, the antimicrobial materials may be applied to the substrate surface using ink jet printing, for example and without limitation.

Referring initially to FIG. 1, a flow diagram 100 of an illustrative embodiment of a method of fabricating an antimicrobial surface coating is shown. In block 102, first and second coating applicator media may be provided. Each of the first and second coating applicator media may include any type of medium which is suitable for applying antimicrobial materials to a surface of a substrate. The first and second coating applicator media may include, for example and without limitation, applicator paint. In some applications, additional coating applicator media may be provided depending on the number of different types of antimicrobial materials which are to be applied to the surface of the substrate.

In block 104, first and second antimicrobial materials of different types may be provided. Each of the first and second antimicrobial materials may be any type of material which is capable of killing microorganisms such as bacteria or fungi, for example and without limitation, and/or destroying or inactivating viruses. In some applications, each of the first and second antimicrobial material may include a biocide (which may be a well-known biocide or a biocide which is currently in research, such as a fullerance), for example and without limitation. In some applications, additional antimicrobial materials may be provided in addition to the first and second antimicrobial materials. The antimicrobial materials may be selected depending on the target range of microorganisms against which antimicrobial action is desired.

In block 106, the first antimicrobial material may be added to the first coating applicator medium and the second antimicrobial material may be added to the second coating applicator medium. In some applications, additional antimicrobial materials may be added to additional coating applicator media, respectively. In some applications, two or more antimicrobial materials may be added to each coating application medium.

In block 108, a substrate having a substrate surface may be provided. The substrate may be any desired material the substrate surface of which is to have antimicrobial properties, including but not limited to plastic; metal; wood; glass; or fabric.

In block 110, the first coating applicator medium with the first antimicrobial material may be applied to the surface of the substrate. In block 112, the second coating applicator medium may subsequently be applied to the surface of the substrate with the second antimicrobial material adjacent to the first antimicrobial material. Additional coating applicator media, each having a selected type of antimicrobial material, may be subsequently applied to the surface of the substrate in successive layers. In some applications, each of the first coating applicator medium and the second coating applicator medium may include two or more antimicrobial materials.

The first coating applicator medium, the second coating applicator medium and any additional coating applicator media may each be applied to the surface of the substrate using any suitable three-dimensional deposition technique which is known to those skilled in the art. Deposition of the coating applicator medium to the substrate may include, for example and without limitation, application by micro-jets; micro-nozzles; micro-dispensers; electrostatic deposition; screen printing; patterned absorption using factors that enhance adherence; or using bio-organisms as carriers. In some applications, the coating applicator media may be applied to the surface of the substrate using an ink jet printing technique, for example and without limitation. The applied coating applicator media with antimicrobial materials may form a multilayered antimicrobial coating on the surface of the substrate. In the antimicrobial coating, the antimicrobial materials of different types may form a three-dimensional pattern in which the antimicrobial materials may be disposed in substantially adjacent and overlapping relationship with respect to each other. In some applications, the antimicrobial materials of different types in the successive layers of the antimicrobial coating may be separated from each other by a spacing of from about 1 micron to about 1 millimeter, for example and without limitation, in the pattern. In block 114, the first, second and any subsequent coating applicator media may be cured. In some applications, two or more antimicrobial materials of different types may be provided in each layer of the antimicrobial coating. The antimicrobial materials in each layer may form separate overlapping, staggered or adjacent patterns.

Referring next to FIGS. 2 and 3, an illustrative embodiment of an antimicrobial structure is generally indicated by reference numeral 1 in top and side views, respectively. The antimicrobial structure 1 may include a substrate 2 (FIG. 3) having a substrate surface 3. The substrate 2 may be any desired material the substrate surface 3 of which is to have antimicrobial properties, including but not limited to plastic; metal; wood; glass; or fabric.

An antimicrobial coating 4 may be provided on the substrate surface 3 of the substrate 2. At least two different types of antimicrobial material may be provided in the antimicrobial coating 4. In the embodiment of the antimicrobial structure 1 which is shown in FIGS. 2 and 3, a first antimicrobial material 8; a second antimicrobial material 9; a third antimicrobial material 10; and a fourth antimicrobial material 11 may be provided in the antimicrobial coating 4. However, in some embodiments the antimicrobial coating 4 may include more than four different types of antimicrobial material depending on the desired range of microorganisms which is to be targeted by the antimicrobial coating 4.

The antimicrobial coating 4 may be applied to the substrate surface 3 in a multi-layered manner as two or more successively-applied coating applicator media, each of which may include at least one selected type of antimicrobial material. Each layer of coating applicator media may include any type of medium which is suitable for applying antimicrobial materials to the substrate surface 3 of the substrate 2. Each layer of coating applicator media may include, for example and without limitation, applicator paint.

As shown in FIGS. 2 and 3, in some embodiments the layers of coating applicator media may be successively deposited on the substrate surface 3 (FIG. 3) in a three-dimensional pattern in which the first antimicrobial material 8 may be disposed generally adjacent to the substrate surface 3 of the substrate 2; the second antimicrobial material 9 may be disposed generally adjacent to the first antimicrobial material 8; the third antimicrobial material 10 may be disposed generally adjacent to the second antimicrobial material 9; and the fourth antimicrobial material 11 may be disposed generally adjacent to the third antimicrobial material 10. The antimicrobial materials 8, 9, 10 and 11 may be disposed in staggered or overlapping relationship with respect to each other when viewed from above as shown in FIG. 2 and when viewed from the side as shown in FIG. 3. In some embodiments, at least two antimicrobial materials of different type, such as the first antimicrobial material 8 and the second antimicrobial material 9, may be disposed together in a first layer, and at least two antimicrobial materials of different type, such as the third antimicrobial material 10 and the fourth antimicrobial material 11, may be disposed together in a second layer, of the substrate surface 3.

In some embodiments, the adjacent antimicrobial materials 8, 9, 10, 11 of different types in the successive layers or the adjacent antimicrobial materials in the same layer of the antimicrobial coating 4 may be separated from each other by a spacing of from about 1 micron to about 1 millimeter, for example and without limitation, in the pattern. Maintaining separation of the antimicrobial materials of different type in the antimicrobial coating 4 may optimize the antimicrobial efficacy of each antimicrobial material. As shown in the example of FIG. 3, deposits of the third antimicrobial material 10 are shown in FIG. 3 as being relatively larger than deposits of the fourth antimicrobial material 11. As shown in the example of FIG. 3, some of the deposits of the fourth antimicrobial material 11 are shown in FIG. 3 as being disposed between deposits of the third antimicrobial material 10. As shown in the example of FIG. 3, some of the deposits of the fourth antimicrobial material 11 are shown in FIG. 3 as being disposed on deposits of the third antimicrobial material 10.

In typical application, the antimicrobial coating 4 is applied to the substrate surface 3 of the substrate 2 typically as was heretofore described. The substrate surface 3 of the substrate 2 may be any surface which is to have antimicrobial properties and may be such a surface in a commercial or military aircraft, rotorcraft or Unmanned Air Vehicle (UAV), for example and without limitation. In aerospace applications, the substrate 2 may be an air duct; lavatory; tray table; bulkhead; or insulation blanket, for example and without limitation. Accordingly, as shown in FIG. 2, each type of antimicrobial material 8, 9, 10, 11 in the antimicrobial coating 4 may kill or inactivate microbes 14 such as bacteria, fungi and/or viruses which fall within the range of microbes 14 acted upon by the antimicrobial material and which contact the antimicrobial coating 4.

Figure 4:
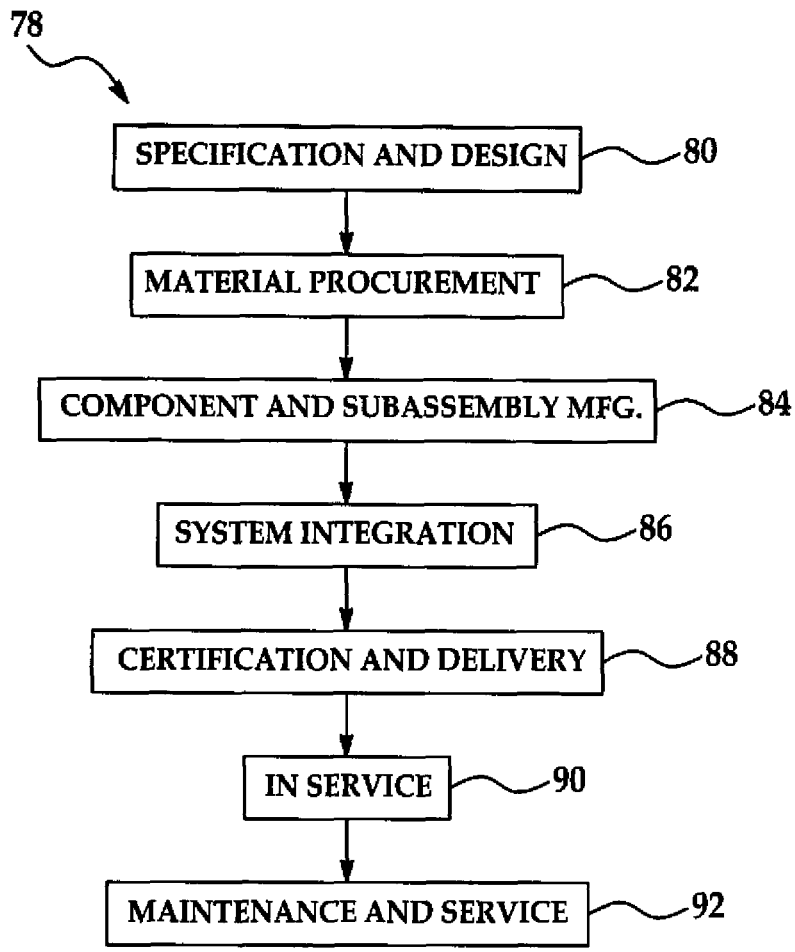
FIG. 4 is a flow diagram of an aircraft production and service methodology.
Figure 5:
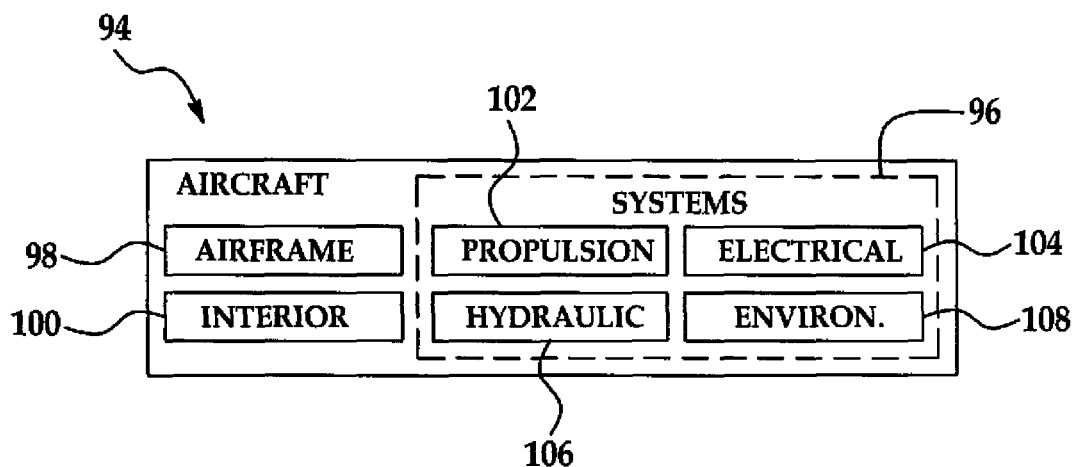
FIG. 5 is a block diagram of an aircraft.

Referring next to FIGS. 4 and 5, embodiments of the disclosure may be used in the context of an aircraft manufacturing and service method 78 as shown in FIG. 4 and an aircraft 94 as shown in FIG. 5. During pre-production, exemplary method 78 may include specification and design 80 of the aircraft 94 and material procurement 82. During production, component and subassembly manufacturing 84 and system integration 86 of the aircraft 94 takes place. Thereafter, the aircraft 94 may go through certification and delivery 88 in order to be placed in service 90. While in service by a customer, the aircraft 94 may be scheduled for routine maintenance and service 92 (which may also include modification, reconfiguration, refurbishment, and so on).

Each of the processes of method 78 may be performed or carried out by a system integrator, a third party, and/or an operator (e.g., a customer). For the purposes of this description, a system integrator may include without limitation any number of aircraft manufacturers and major-system subcontractors; a third party may include without limitation any number of vendors, subcontractors, and suppliers; and an operator may be an airline, leasing company, military entity, service organization, and so on.

As shown in FIG. 5, the aircraft 94 produced by exemplary method 78 may include an airframe 98 with a plurality of systems 96 and an interior 100. Examples of high-level systems 96 include one or more of a propulsion system 102, an electrical system 104, a hydraulic system 106, and an environmental system 108. Any number of other systems may be included. Although an aerospace example is shown, the principles of the invention may be applied to other industries, such as the automotive industry.

The apparatus embodied herein may be employed during any one or more of the stages of the production and service method 78. For example, components or subassemblies corresponding to production process 84 may be fabricated or manufactured in a manner similar to components or subassemblies produced while the aircraft 94 is in service. Also, one or more apparatus embodiments may be utilized during the production stages 84 and 86, for example, by substantially expediting assembly of or reducing the cost of an aircraft 94. Similarly, one or more apparatus embodiments may be utilized while the aircraft 94 is in service, for example and without limitation, to maintenance and service 92.

Although the embodiments of this disclosure have been described with respect to certain exemplary embodiments, it is to be understood that the specific embodiments are for purposes of illustration and not limitation, as other variations will occur to those of skill in the art.

What is claimed is:

1. A method of fabricating an antimicrobial surface coating, comprising:
   providing a substrate;
   separately providing a first staggered pattern of a first antimicrobial material on the substrate, the first antimicrobial material being configured to inactivate a first target range of microorganisms; and
   separately providing a second staggered pattern of a second antimicrobial material on the substrate, the second antimicrobial material being configured to inactivate a second target range of microorganisms, the first target range of microorganisms being different than the second target range of microorganisms, the first antimicrobial material being different than the second antimicrobial material, wherein the second staggered pattern to at least partially overlap the first staggered pattern, and the second staggered pattern to be at least partially disposed in spaces defined by the first staggered pattern.

2. The method of claim 1, wherein the second antimicrobial material is to be spaced at least about 1 micron from the first antimicrobial material.

3. The method of claim 1, wherein the second antimicrobial material is to be spaced about 1 micron to about 1 millimeter from the first antimicrobial material.

4. The method of claim 1, wherein providing the first staggered pattern of the first antimicrobial material comprises providing a first coating applicator medium, adding the first antimicrobial material to the first coating applicator medium, and applying the first coating applicator medium to the substrate.

5. The method of claim 4, wherein providing the second staggered pattern of the second antimicrobial material comprises providing a second coating applicator medium, adding the second antimicrobial material to the second coating applicator medium, and applying the second coating applicator medium adjacent the substrate.

6. The method of claim 5, wherein applying the first coating applicator medium and applying the second coating applicator medium comprises applying the first coating applicator medium and the second coating applicator medium using a three-dimensional printing technique.

7. The method of claim 6, wherein applying the first coating applicator medium and the second coating applicator medium comprises applying the first coating applicator medium and the second coating applicator medium using ink jet printing.

8. The method of claim 1, wherein providing the second staggered pattern of the second antimicrobial material comprises providing the second antimicrobial material in staggered relationship with respect to the first antimicrobial material.

9. A method of fabricating an antimicrobial surface coating, comprising:
separately providing a first staggered pattern of first antimicrobial materials comprising first deposits on a substrate; and
separately providing a second staggered pattern of second antimicrobial materials comprising second deposits on the substrate, the first antimicrobial materials being different than the second antimicrobial materials, the first deposits being differently sized than the second deposits, the second staggered pattern to at least partially overlap the first staggered pattern, and the second staggered pattern to be at least partially disposed in spaces defined by the first staggered pattern.

10. The method of claim 9, wherein providing the second staggered pattern of the second antimicrobial materials comprises providing one or more of the second antimicrobial materials at a spacing of at least about 1 micron with respect to one or more of the first antimicrobial materials.

11. The method of claim 9, wherein providing the second staggered pattern of the second antimicrobial materials comprises providing one or more of the second antimicrobial materials at a spacing of from about 1 micron to about 1 millimeter with respect to one or more of the first antimicrobial materials.

12. The method of claim 9, wherein providing the first staggered pattern of the first antimicrobial materials on the substrate comprises providing a first coating applicator medium, adding the first plurality of antimicrobial materials to the first coating applicator medium, and applying the first coating applicator medium to the substrate.

13. The method of claim 12, wherein providing the second staggered pattern of the second antimicrobial materials comprises providing a second coating applicator medium, adding the second antimicrobial materials to the second coating applicator medium, and applying the second coating applicator medium adjacent the substrate.

14. The method of claim 13, wherein applying the first coating applicator medium and applying the second coating applicator medium comprises applying the first coating applicator medium and the second coating applicator medium using a three-dimensional printing technique.

15. The method of claim 14, wherein applying the first coating applicator medium and the second coating applicator medium comprises applying the first coating applicator medium and the second coating applicator medium using ink jet printing.

16. The method of claim 9, wherein providing the second staggered pattern of second antimicrobial materials comprises providing the second antimicrobial materials in staggered relationship with respect the first antimicrobial materials.

17. An antimicrobial structure, comprising:
a substrate;
a first antimicrobial material on the substrate in a first staggered pattern; and
a second antimicrobial material on the substrate in a second staggered pattern, the first antimicrobial material and the second antimicrobial material being separately deposited on the substrate, the first antimicrobial material being different than the second antimicrobial material, wherein the second staggered pattern is to at least partially overlap the first staggered pattern, the second staggered pattern to be at least partially disposed in spaces defined by the first staggered pattern.

18. The antimicrobial structure of claim 17, wherein the second antimicrobial material is disposed at a spacing of at least about 1 micron with respect to the first antimicrobial material.

19. The antimicrobial structure of claim 17, wherein the second antimicrobial material is disposed at a spacing of from about 1 micron to about 1 millimeter with respect to the first antimicrobial material.

20. The antimicrobial structure of claim 17, wherein at least some of the second antimicrobial material is disposed in generally staggered and overlapping relationship with respect to at least some of the first antimicrobial material.

21. The method of claim 1, wherein the substrate comprises a surface of an aircraft.

22. The method of claim 1, wherein the substrate comprises a surface of a vehicle.

* * * * *